US006932984B1

(12) United States Patent
Babtsov et al.

(10) Patent No.: US 6,932,984 B1
(45) Date of Patent: Aug. 23, 2005

(54) METHOD OF MICROENCAPSULATION

(75) Inventors: Vladimir Babtsov, Kiryat Shmona (IL); Yury Shapiro, Givat Shmuel (IL); Emma Kvitnitsky, Kiryat Shmona (IL)

(73) Assignee: Tagra Biotechnologies Ltd., Misgav (IL)

( * ) Notice: Subject to any disclaimer, the term of this patent is extended or adjusted under 35 U.S.C. 154(b) by 76 days.

(21) Appl. No.: 10/130,529

(22) PCT Filed: Nov. 16, 2000

(86) PCT No.: PCT/IL00/00759

§ 371 (c)(1),
(2), (4) Date: Sep. 30, 2002

(87) PCT Pub. No.: WO01/35933

PCT Pub. Date: May 25, 2001

(30) Foreign Application Priority Data

Nov. 17, 1999 (GB) .................................. 9927202

(51) Int. Cl.[7] .......................... A61K 9/16; A61K 9/50; B05D 7/00; B01J 13/02; B32B 15/02
(52) U.S. Cl. ...................... 424/490; 264/4.33; 264/4.6; 427/212; 427/213.3; 427/213.36; 428/402.2; 428/402.21; 428/402.22; 428/402.24; 523/105; 424/493; 424/494; 424/495; 424/497; 424/501
(58) Field of Search ........................ 523/105; 424/501, 424/490, 493, 494, 495, 497; 428/402.21, 428/402.22, 402.2, 402.24; 264/4.6, 4.33; 427/212, 213.3, 213.36

(56) References Cited

U.S. PATENT DOCUMENTS

| 3,737,337 | A | 6/1973 | Schnoring et al. |
| 3,891,570 | A | 6/1975 | Fukushima et al. |
| 3,951,851 | A | 4/1976 | Kitajima et al. |
| 4,384,975 | A | 5/1983 | Fong |
| 5,916,598 | A | 6/1999 | Pickey et al. |

FOREIGN PATENT DOCUMENTS

FR    2 766 368    1/1999

*Primary Examiner*—Patrick D. Niland
(74) *Attorney, Agent, or Firm*—Browdy and Neimark, P.L.L.C.

(57) ABSTRACT

A method for microencapsulation of substances is provided. The substance(s) is/are dissolved or dispersed in an organic solvent of the kind that is partially miscible in water media. This organic solution is then mixed with an aqueous solution, which is saturated with an organic solvent and an emulsifier to form an emulsion. The emulsion is then poured into water under continuous agitation for the extraction of residual solvent. The formation of the solid capsules takes place during this extraction process. The capsules are undergone to further purification, whereby the microcapsules can be separated from the water and dried. By conditions of incubation of microcapsules in water-containing formulations the wall-softening process takes place. The unique system for controlled releasing the ingredients from microcapsules is based on the above-mentioned process.

20 Claims, No Drawings

US 6,932,984 B1

METHOD OF MICROENCAPSULATION

REFERENCE TO RELATED APPLICATIONS

The present application is the national stage under 35 U.S.C. §371 of international application PCT/IL00/00759, filed Nov. 16, 2000, which designated the United States, and which international application was published under PCT Article 21(2) in the English language.

FIELD OF THE INVENTION

This invention relates to a method of microencapsulation of cosmetic ingredients, vitamins and pharmaceutical substances.

BACKGROUND OF THE INVENTION

Microcapsules are available usually in powder form and consist of spherical particles, which contain an encapsulated (entrapped) substance. The spherical particle usually consists of a polymeric shell and the encapsulated active product is located within the shell. The polymeric shell is frequently applied as a wall-forming material, and serves as a membrane for the encapsulated substance. This membrane is semi-permeable and allows the microcapsule to be an efficient tool for controlled release applications.

Microencapsulation itself has various advantages. Microcapsules protect sensitive substances from degradation processes and provide means for controlled release of desired active substances. It also enables the conversion of liquids to powders and is used to separate substances, which are harmful upon contact with each other.

Numerous techniques for microencapsulation are available depending on the nature of the encapsulated substance and on the type of polymer used. A widely used method for the encapsulation of water insoluble drugs within water insoluble polymers is the solvent removal method. Generally in such a process, the desired polymer is dissolved in a suitable organic solvent. This action is followed by the addition of the desired substance to be encapsulated. This substance is either dissolved or dispersed in the organic solvent. The resulting organic solution/dispersion is dispersed in an aqueous phase to obtain an-oil-in-water emulsion where oily microparticles are dispersed in the aqueous phase. Upon complete removal of the solvent from the microparticles the microcapsules are formed. Several patents describe methods of removing the solvent. U.S. Pat. No. 4,384,975 describes the removal of the solvent by vacuum distillation. In GB 1,394,780 the removal of the solvent is done by evaporation. In U.S. Pat. No. 3,891,570 the removal of the polymer solvent is carried out by heating the aqueous dispersion or by reducing its pressure. In U.S. Pat. No. 3,737,337 the removal of the organic solvent is done by extraction with water, however-it is limited to certain solvent systems. U.S. Pat. No. 5,916,598 describes a method for the preparation of slow-release biodegradable, biocompatible microparticles using the general technique of solvent removing, and microparticles comprising microencapsulated active agent.

Microencapsulation is suitable for drugs, vitamins and food supplements since this process is easily adaptable by varying the solvents and/or the polymers. It may yield microcapsules having desirable size, round shape and smooth surface that are important for controlled release and for the chemical stability of the core material.

A basic prerequisite for this process is the use of a solvent that is able to dissolve efficiently the substance to be encapsulated as well as the wall-forming material. This solvent has to be only partially soluble in water, giving rise to emulgation of an organic phase in a continuous water phase. Chlorinated solvents such as dichloromethane, chloroform, or their mixtures with other solvents are widely used since they facilitate the microencapsulation process.

However all the microencapsulating technologies based on solvent systems such as chlorinated solvents are not applicable for food, cosmetic and pharmaceutical applications, since they do not meet FDA and other regulations due to the presence of residual amounts of chlorinated solvents in the microcapsules. Simple vacuum or heat drying do not result in a sufficiently low chlorinated solvent content so as to meet FDA regulations, thus creating an essential necessity for a method for encapsulating vitamins, food supplements, oils or pharmaceuticals by the solvent removal technique.

SUMMARY OF THE INVENTION

It is an object of the present invention to provide a method for encapsulating vitamins, food supplements, oils or pharmaceuticals by the solvent removal technique, which is easily adapted to a desired encapsulated principle.

It is a further object of the present invention to provide a microencapsulating process by using non-chlorinated, physiologically acceptable solvents.

The present invention thus provides a method for the microencapsulation of a substance, comprising the stages of:

(a) dissolving or dispersing the substance together with a wall-forming material in an organic solvent of a kind that is partially miscible in water, to form an organic solution or dispersion;

(b) mixing said organic solution or dispersion with an aqueous solution, said aqueous solution being saturated with said organic solvent dissolved therein and comprising an emulsifier, to form an emulsion;

(c) while agitating, pouring said emulsion into water to form a (d) Adding an excess amount of water to initiate extraction of the organic solvent from the emulsion;

(e) incubating for a time sufficient to allow formation of microcapsules in the mixture; and (f) further removal of the residual amount of organic solvent in said formed micrcapsules by immersing them in an alcoholic aqueous solution.

Optionally, the mixture is further treated after stage (f) to isolate the microcapsules. This may be done by filtration, centrifugation, washing, evaporation, liophilization, etc., as generally known per se.

In step (d) the excess amount of water is generally an excess of between about 20:1 to about 50:1 (v/v).

The term "wall-forming material" used above refers to material, which subsequently forms a component of the external walls or layer of the microcapsules. The wall-forming material may be a single type of material or may be a combination of the two or more different materials. The wall-forming material is typically a polymer or a combination of two or more different polymers.

The term "partially miscible in water" should be understood as relating to the property of being able to be dissolved in water in concentrations while lower than a certain critical concentration, while the concentration thereof increases above a certain critical value, there is phase separation and the water and the organic solvents form two separate phases. An example of such an organic solvent is ethyl acetate or ethyl formate.

The term "saturated" should be understood as referring to a solution that contains the organic solvent in a concentration about the critical value or slightly below, namely, a saturated solution contains a concentration of the organic solvent close to the maximal concentration before phase separation occurs. However, the term "saturated" should not be understood in a limiting fashion in that at times, also a solution containing less than 90%, and at times even about 80% of the critical concentration may be considered as saturated for the purpose of the invention. The emulsifier used in stage (b) may either be a priori dissolved in the aqueous solution or may be added to the aqueous solution simultaneously or after mixing of the organic solution therewith.

The term "agitation" should be understood as referring to steering, shaking, vibrating and in general to any process whereby mechanical energy is transferred to the liquid to cause some turbulence in the liquid.

The term "water" used in stage (c) should be understood as referring either to pure water, or to an aqueous solution such as a salt solution.

The incubation in stage (e) is typically for 3–10 min., although it will be understood that the invention is not limited to incubation at this time range and that at times, incubation may be below or above the aforementioned time range.

The microcapsules produced in accordance with the invention may have different, wide ranging applications, depending on the exact nature of the substance incorporated therein as well as on the release properties of the substance which is controlled by the wall-forming material which imparts the characteristics of the microcapsules' wall. Example of uses is applied in dermal formulations, where said substance is dermal active. As will be appreciated, the invention is not limited by the intended use of the microcapsules or the nature of the substance encapsulated therein.

The invention also provides novel microcapsules prepared by the above-mentioned method and those compositions comprising such microcapsules.

DETAILED DESCRIPTION OF THE INVENTION

In recent years there is an increasing interest in introducing vitamins such as A, C, E and F (which are essentially unsaturated fatty acids) into cosmetic, dermatological, feed supplements and food additives. Vitamin C enables the growth of connective tissues and stimulates reproduction of collagen. Vitamin E is known as an antioxidant and as a scavenger of free radicals. Vitamin A combats aging efficiently. Thus, these vitamins may be used in skin and hair care for treating phenomenon related to aging, pigmentation, dryness or skin disease, e.g., such as psoriasis. These vitamins are also favorable to the restructuring of the skin. It is known that these vitamins are very unstable in solution and are sensitive to various factors, which result in their fast decomposition and loosing of biological activity when unprotected. The products of decomposition or oxidation of vitamins possess the negative biological effects such as irritation, prooxidant activity, etc. Encapsulating these vitamins is a suitable mean for protecting them while retaining their biological efficacy. However, in order to be suitable for the above-mentioned use, microcapsules containing vitamins should not contain any remaining harmful solvents.

Another important feature required from microcapsules is being able to effectively control the release of the active components from the microcapsules.

In the method proposed in the present invention all materials were recognized by the FDA as having GRAS status, i.e. were generally recognized as safe. The benefit of using such materials is that the final product, microcapsules, are biocompatible and suitable for both internal and external use.

It was found by the present invention that the rapid extraction of the organic solvent upon mixing of the organic phase with the aqueous phase is prevented, thus leading to the formation of desired, uniform microcapsules. This effect is achieved by saturation of the aqueous phase with the organic solvent used for dissolving the wall-forming material and the substance to be encapsulated. It appears that water saturated with the same solvent cannot extract the solvent from the organic phase, and thus microdroplets of organic phase have enough time to be formed and the resulting spherical microcapsules are obtained. They are converted into hard microcapsules after slow solvent extraction by water.

The present invention affords the production of uniform microcapsules containing a high loading of oil soluble substances of up to 70%.

These microcapsules have spherical shape, and altering the process parameters can control smooth surface and their size from 3 to 300 $\mu$m. The microcapsules made according to the present invention can be effectively used in topical applications due to the unique ability of the capsules' walls to soften and then to control release of active substances to target area directly. The spherical shape and the uniform size of the microcapsules guarantee the homogenous distribution of active substances on the skin.

In the present invention the method of preparing the microcapsules includes the following stages. In the first stage, an organic solvent that is capable of dissolving or dispersing the oil soluble or the oil non-soluble substance and the wall-forming material is chosen. The solvent can be selected from a variety of solvents such as ethyl acetate, ethyl formate or other appropriate solvents approved by the FDA, or their mixtures. The solvent should be inactive with the dissolved material. The substance to be encapsulated by the present process is then dissolved and optionally can also be dispersed in the organic solvent to form an organic solution or dispersion. The substance can be either a solid or a liquid. A wall-forming material is then dissolved in the organic solution/dispersion. An appropriate wall-forming polymeric material is chosen from the group of polyacrylates such as polyacrylic acid polymethacrylates such as poly(methylmethacrylate), poly(n-butylmethacrylate), Eudragit RSPO, cellulose ethers such as ($C_{1-4}$alkyl)cellulose, or cellulose esters such as cellulose acetate.

In the second stage an aqueous continuous phase is saturated by the same organic solvent (or mixture of solvents) used in the first stage. An appropriate emulsifier is added to the aqueous phase. Such an emulsifier may be selected from poly(vinylalcohol), sodium lauryl sulfate, lauryl phosphate, ethoxylated sorbates such as Tween-80, polyglycerol and poly(ethylene glycol), and their esters and ethers. Said added emulsifier should be chosen and adapted to the system in such a way that it does not separate from water after the organic solvent is added in the next stage. It is advisable to adjust the pH of the aqueous phase to be slightly acidic so as to prevent the hydrolysis of ethyl acetate or any other ester containing solvent.

In the third stage the organic solution/dispersion obtained in the first stage, which contains the substance and the wall-forming material, is poured into the aqueous continuous phase saturated with the organic solvent used in the first stage, forming an emulsion. The pouring is done with agitation and the agitation is continued for a further period of time. The rate of mixing and its duration affect, among other factors, the size of the formed droplets. Other factors, which are responsible for the size of the formed droplets, are the ratio of water to organic phase, temperature, quantity and kind of emulsifier.

In the fourth stage, water is added to the emulsion formed in the previous stage, for extracting the organic solvent. Preferably, the quantity of the water added is 10–30 times higher than the whole quantity of the organic solvent in the mixture. The most preferable ratio is 20:1. Following the addition of the water, the mixture is agitated for several minutes up to a point where the main amount of the organic solvent is extracted into the water and equilibrium is reached. Typically it takes 3–10 minutes to reach equilibrium. Upon the gradual removal of the organic solvent solid microcapsules are formed. The formed microcapsules are then isolated by filtration or centrifugation, subsequently washed with water and dried.

Although, the FDA recognizes ethyl acetate and similar solvents as safe solvents, it is necessary sometimes to remove even trace amounts of such solvents (for example, because of odor).

Evaporating the solvent from the dispersion after the fourth stage (wet microcapsules) is not applicable for delicate and sensitive compounds such as used in the present invention. It should also be understood, that solvent evaporation from dried microcapsules is not effective, since diffusion of solvent through a hard polymer wall is very slow, and the odor of the solvent may be felt even after keeping under vacuum for several days.

In order to remove trace amounts of the solvent the present invention presents a new effective extraction technique. The microcapsules obtained after filtration are immersed in a 5% solution of ethanol in water for 2–12 hours thereby causing the organic solvent to be extracted from the microcapsules. Under such conditions the organic solvent (for example, ethyl acetate) present within the microcapsule migrates from the microcapsules to the outer medium rapidly, and the remaining amount of solvent in the microcapsules is well within the allowed CTFA and FDA range.

The microcapsules of the present invention, among other uses are intended for cosmetic and dermatological applications. Such a use requires a unique design of the microcapsules with respect to their mechanical properties. While the microcapsules have to be on the one hand soft enough to rupture upon rubbing on skin they must also be hard enough on the other hand to avoid destruction of shell and realization of the content during technological process by isolation, drying, sieving, etc.

Such mechanical properties are achieved by choosing an appropriate wall forming material. The preferred wall forming material is poly(methyl-methacrylate) (PMMA) having a rather low molecular weight and containing 17% of free carboxylic groups. In addition, selection of a suitable plasticizer and determining its percentage are another important factor. The plasticizer may be selected from mineral oils, silicon oils or triglycerides of fatty acids. The presence of the plasticizer in the microcapsules of the present invention affects their mechanical properties thus positively affecting their dermal use and efficiency. This special composition enables microcapsules to remain intact during handling and become soft after 1–2 days incubating inside a cosmetic or dermatological formulation. These microcapsules may then rupture completely upon being rubbed on skin thereby releasing their contents.

The proposed process can effectively be used for producing double-layered microcapsules, where the outer layer completely and almost uniformly covers an inner core. This technique was successfully used for preparing microencapsulated pigments for make-up, where core containing, for example, brown pigment, was covered by the titanium dioxide layer, and for masking with concurrent protection unstable and/or colored substances.

On an industrial scale production, after separation of microcapsules, the organic phase may be removed from the water phase by distillation. Thus, both the water and organic phase can be recycled.

Having generally described the invention, a further understanding can be obtained by reference to certain specific examples, which are provided herein for a purpose of illustration only and are not intended to be limiting unless otherwise specified.

EXAMPLES

Example 1

A Process for Encapsulation of Oil

An aqueous phase was prepared as follow: 0.5 g of sodium lauryl sulfate was dissolved in 50 ml of tap water saturated with 6 ml of ethyl acetate. An organic phase was prepared by dissolving 0.7 g oil and 0.3 g ethyl cellulose in 5 ml of ethyl acetate. The resulting organic phase was poured into the aqueous phase while stirring and then 100 ml of fresh water were added. After microcapsules were formed during a period of about 3–10 minutes, they were filtered, washed by water and dried at the temperature no higher 20° C. An average diameter of the microcapsules was 70 $\mu$m. Efficiency of encapsulation reached was 99%.

Example 2

A Process for Encapsulation of Vitamin F

An aqueous phase was prepared as in example 1. The pH of the aqueous phase was further adjusted to 3 by citric acid. An organic phase was prepared by dissolving 0.25 g vitamin F in a mixture of natural triglycerides of fatty acids, 0.0 $\mu$g antioxidant that can be chosen from butylated hydroxyanisole (BHA), butylated hydroxytoluene (BHT) or tocopherol (vitamin E) and 0.74 g poly(methyl) metacrylate (PMMA) in 5 ml of ethyl acetate.

The resulting organic phase was poured into the aqueous phase while stirring and then 100 ml of fresh water were added. The resulting microcapsules formed were filtered, washed by water and dried at the temperature no higher 20° C. An average diameter of the microcapsules was 50 $\mu$m.

Example 3

A Process for Encapsulation of Vitamin E

The preparations of the aqueous and organic phases were done in the same manner as in example 2, vitamin E (tocopherol) rather than vitamin F being dissolved in the organic phase. The resulting organic phase was poured into the aqueous phase while stirring and then 100 ml of fresh water were added. The resulting microcapsules formed were filtered, washed by water and dried at the temperature no higher 20° C. An average diameter of the microcapsules was 100 µm.

Example 4

A Process for Encapsulation of Vitamin A Palmitate

An aqueous phase was prepared by dissolving 0.5 g of poly(vinyl alcohol) in 50 ml water saturated by 6 ml of ethyl acetate. An organic phase was prepared by dissolving 0.075 g retinol palmitate, 0.1 g mineral oil, 0.01 g of an antioxidant (chosen from BHA, BHT, tocopherol or their mixture) and 0.815 g PMMA in 5 ml of ethyl acetate. The organic phase was poured into the aqueous phase while stirring and then 100 ml of fresh water were added. The microcapsules formed were filtered, washed by water and dried at the temperature no higher 20° C. An average diameter of the microcapsules was 40 µm.

Example 5

A Process for Encapsulating a Suspension of Vitamin C

An aqueous phase was prepared by saturating 100 ml water containing 0.08% sodium lauryl sulphate by 12 ml ethyl acetate.

Separately an organic phase was prepared: 0.5 g of finely grounded vitamin C (particle size 5–10 micron) were added to a solution of 2 g PMMA in 10 ml ethyl acetate. After the addition, the batch was dispersed by sonication.

Organic phase was poured into the aqueous phase, and homogenated. Then 400 ml of fresh water, containing 0.08% sodium lauryl sulphate were added for the extraction of the ethyl acetate and mixing was continued for several min. Formed microcapsules were separated by sedimentation, washed by water and dried.

Example 6

A Process for Encapsulation of a Mixture of Vitamins A and E

An organic phase was prepared as follows: 0.075 g vitamin A palmitate, 0.25 g of vitamin E and 0.675 g of PMMA were dissolved in ethyl acetate. An aqueous phase was prepared as described in example 4. Then mixing of phases, dilution by water, formation of microcapsules and their isolation were done as described in example 4.

Example 7

A Process for Encapsulation of Pigments into Double-Layered Microcapsules.

At the first step, the inner core microcapsules were prepared as follows. 2 g of mixed iron oxides (brown pigment) were sonicated for 1 min in 8 ml of an ethyl acetate solution containing 0.25 g poly(styrene/maleic anhydride) and 0.25 g of sodium cocoyl lactylate as surfactant. This suspension was emulgated in 100 ml 0.5% water solution of PVA, which was preliminary saturated by ethyl acetate. This emulsion was poured into 1000 ml fresh water during agitation to extract ethyl acetate. The formed microcapsules were isolated by sedimentation, filtered and washed by fresh water.

The microcapsules obtained were immersed into 0.50 ml 5% sodium carbonate solution and incubated at 40° C. for one hour to enable hydrolysis of the maleic anhydride groups. This treatment is sufficient to alter the surface of the microcapsules in a way, which prevents dissolution of microcapsules in ethyl acetate at the second step of process. The microcapsules were washed finally by fresh water and dried.

In the second step the microcapsules containing the brown pigment were covered by titanium dioxide. Thus 0.8 g of titanium dioxide were sonicated in 3 ml of ethyl acetate solution of Eudragit RSPO, a copolymer of ethyl acrylate, methyl methacrylate, and trimethylammoniummethyl methacrylate, (ROHM, Germany) and 0.1 g diethyl phthalate (DEP). 0.3 g of the microcapsules containing the brown pigment was added to this dispersion during agitation. After a homogeneous suspension was obtained it was poured into 50 ml of 0.5% water solution of PVA during agitation. The obtained emulsion was poured into 500 ml fresh water, and agitated for 3 min to extract ethyl acetate. The obtained microcapsules were isolated by sedimentation, filtered, washed by water and dried.

Under microscopic observation, microcapsules look like white separate spherical particles with smooth surface. After applying on skin, white microcapsules broke down and released the brown pigment.

Example 8

A Process for Microencapsulation of Flavonoids 0.1 g of flavonoids and 1 g of titanium dioxide were suspended in 4 ml solution of 0.2 g Eudragit RSPO (ROHM, Germany) in ethyl acetate. This suspension was emulgated in 50 ml water solution of PVA, saturated by ethyl acetate. The resulting emulsion was poured into 500 ml of fresh water while agitating in order to extract ethyl acetate. Microcapsules obtained were by sedimentation, filtered, washed by water and dried at the temperature no higher 20° C. An average diameter of the microcapsules was 100 µm.

What is claimed is:

1. A method for the production of microcapsules for dermal application, wherein the microcapsules consist of a polymer shell and a core made of an encapsulated substance, said method comprising the steps of:
   (a) dissolving or dispersing the substance in an organic solvent of a kind that is partially miscible in water and is capable of dissolving or dispersing said substance, together with a wall-forming polymeric material selected from the group consisting of a polyacrylate, a polymethacrylate, a cellulose ether, a cellulose ester, and poly(styrene-co-maleic anhydride), to form an organic solution or dispersion;
   (b) preparing an aqueous continuous phase saturated with said organic solvent and comprising an emulsifier;
   (c) while agitating, pouring the organic solution or dispersion obtained in (a) into the aqueous continuous phase obtained in (b), to form an emulsion;
   (d) adding an excess amount of water to the emulsion obtained in (c) for extraction of the organic solvent from the emulsion, thus forming solid microcapsules; and
   (e) either (i) isolating the microcapsules, washing with water, and drying at a temperature not higher than 20°

C., or (ii) immersing the microcapsules in an aqueous solution of alcohol, separating the microcapsules, and drying at a temperature not higher than 20° C.

2. The method according to claim 1, wherein said substance is selected from the group consisting of an oil, an oil-soluble vitamin, an oil non-soluble vitamin, a pigment, a natural extract, a pharmaceutical, and mixtures thereof.

3. The method according to claim 2, wherein said oil-soluble or oil non-soluble vitamin is selected from the group consisting of vitamin A, B, C, D, E, F, K, and mixtures thereof.

4. A method for the production of microcapsules for dermal application, wherein the microcapsules consist of a polymer shell and an core made of an encapsulated pigment, said pigment being selected from the group consisting of mixed iron oxides (brown pigment), titanium dioxide, and mixtures thereof, said method comprising the steps of:
  (a) dispersing the pigment in an organic solvent of a kind that is partially miscible with water and is capable of dissolving or dispersing said pigment, together with a wall-forming polymeric material selected from the group consisting of a polyacrylate, a polymethacrylate, a cellulose ether, a cellulose ester, and poly(styrene-co-maleic anhydride), to form an organic solution or dispersion;
  (b) preparing an aqueous continuous phase saturated with said organic solvent and comprising an emulsifier;
  (c) while agitating, pouring the organic dispersion obtained in (a) into the aqueous continuous phase obtained in (b), to form an emulsion;
  (d) while agitating, adding an excess amount of water to the emulsion obtained in (c) for extraction of the organic solvent from the emulsion, thus forming solid microcapsules; and
  (e) either (i) isolating the microcapsules, washing with water, and drying at a temperature not higher than 20° C., or (ii) immersing the microcapsules in an aqueous solution of alcohol, separating the microcapsules, and drying at a temperature not higher than 20° C.

5. The method according to claim 2, wherein said substance is at least one flavonoid.

6. The method according to claim 1, wherein said organic solvent partially miscible with water is an organic solvent approved for dermatological application.

7. The method according to claim 6, wherein said organic solvent is selected from the group consisting of ethyl acetate, ethyl formate, and mixtures thereof.

8. The method according to claim 1, wherein said polymethacrylate is selected from the group consisting of poly(methylmethacrylate), poly(n-butylmethacrylate) and a copolymer of ethyl acrylate, methyl methacrylate and trimethylammoniummethyl methacrylate.

9. The method according to claim 1, wherein said emulsifier of step (b) is selected from the group consisting of polyvinyl alcohol, sodium lauryl sulfate, lauryl phosphate, sodium cocoyl lactylate, an ethoxylated sorbate, polyglycerol, poly(ethylene glycol), and their esters and ethers.

10. The method according to claim 1, wherein the amount of added water in step (d) is 10–30 times higher than the whole quantity of the organic solvent in the mixture, optionally at the ratio of 20:1.

11. The method according to claim 1, wherein in step (e)(ii) the microcapsules are immersed in an aqueous solution of alcohol consisting of a 5% solution of ethanol in water, for 2–12 hours.

12. Microcapsules consisting of a polymer shell and a core made of an encapsulated substance for cosmetic and dermatological applications, wherein said microcapsules are obtained according to a method comprising the steps of:
  (a) dissolving or dispersing the substance in an organic solvent of a kind that is partially miscible with water and is capable of dissolving or dispersing said substance, together with a wall-forming polymeric material selected from the group consisting of a polyacrylate, a polymethacrylate, a cellulose ether, a cellulose ester, and poly(styrene-co-maleic anhydride), to form an organic solution or dispersion;
  (b) preparing an aqueous continuous phase saturated with said organic solvent and comprising an emulsifier;
  (c) while agitating, pouring the organic solution or dispersion obtained in (a) into the aqueous continuous phase obtained in (b), to form an emulsion;
  (d) adding an excess amount of water to the emulsion obtained in (c) for extraction of the organic solvent from the emulsion, thus forming solid microcapsules; and
  (e) either (i) isolating the microcapsules, washing with water, and drying at a temperature not higher than 20° C., or (ii) immersing the microcapsules in an aqueous solution of alcohol, separating the microcapsules, and drying at a temperature not higher than 20° C.

13. Microcapsules according to claim 12 which are soft enough to rupture upon rubbing on the skin thereby releasing their contents but hard enough to remain intact and avoid release of their contents during isolation, drying and sieving carried out in step (e).

14. Microcapsules according to claim 12, further comprising a plasticizer.

15. Microcapsules consisting of a polymer shell and a core made of an encapsulated substance for cosmetic and dermatological applications, obtained according to a method comprising the steps of:
  (a) dissolving or dispersing the substance in an organic solvent of a kind that is partially miscible with water and is capable of dissolving or dispersing said substance, together with a wall-forming polymeric material selected from the group consisting of a polyacrylate, a polymethacrylate, a cellulose ether, a cellulose ester, and poly(styrene-co-maleic anhydride), to form an organic solution or dispersion;
  (b) preparing an aqueous continuous phase saturated with said organic solvent and comprising an emulsifier;
  (c) while agitating, pouring the organic solution or dispersion obtained in (a) into the aqueous continuous phase obtained in (b), to form an emulsion;
  (d) adding an excess amount of water to the emulsion obtained in (c) for extraction of the organic solvent from the emulsion, thus forming solid microcapsules; and
  (e) either (i) isolating the microcapsules, washing with water, and drying at a temperature not higher than 20° C., or (ii) immersing the microcapsules in an aqueous solution of alcohol, separating the microcapsules, and drying at a temperature not higher than 20° C., said microcapsules further comprising a plasticizer, wherein said plasticizer is selected from the group consisting of mineral oils, silicon oils and triglycerides of fatty acids.

16. Microcapsules for cosmetic and dermatological applications, which are double-layered microcapsules, where the outer layer completely and almost covers an inner core consisting of a polymer shell and a core made of an encapsulated substance, wherein said double-layered microcapsules are obtained according to a method comprising the steps of:

(a) dissolving or dispersing the substance in an organic solvent of a kind that is partially miscible with water and is capable of dissolving or dispersing said substance, together with a wall-forming polymeric material selected from the group consisting of a polyacrylate, a polymethacrylate, a cellulose ether, a cellulose ester, and poly(styrene-co-maleic anhydride), to form an organic solution or dispersion;

(b) preparing an aqueous continuous phase saturated with said organic solvent and comprising an emulsifier;

(c) while agitating, pouring the organic solution or dispersion obtained in (a) into the aqueous continuous phase obtained in (b), to form an emulsion;

(d) while agitating, adding an excess amount of water to the emulsion obtained in (c) for extraction of the organic solvent from the emulsion, thus forming solid microcapsules;

(e) either (i) isolating the microcapsules, washing with water, and drying at a temperature not higher than 20° C., or ii) immersing the microcapsules in an aqueous solution of alcohol, separating the microcapsules, and drying at a temperature not higher than 20° C.; and (f) covering the microcapsules with an outer layer by repeating steps (a) to (e) with a second substance, thus obtaining the double-layered microcapsules, where the outer layer completely and almost covers an inner core consisting of a polymer shell and a core made of an encapsulated substance.

17. Double-layered microcapsules according to claim 16 comprising pigments for make-up, wherein an inner core of brown pigment is covered by a titanium dioxide layer.

18. Composition for skin care, skin supplement or sun care comprising microcapsules according to claim 12.

19. Composition comprising microcapsules according to claim 12 wherein the encapsulated substance is a color cosmetic or a cosmeticeutical.

20. Composition for oral hygiene or oral care comprising microcapsules according to claim 12.

* * * * *